United States Patent
Lu et al.

(10) Patent No.: US 6,785,640 B1
(45) Date of Patent: Aug. 31, 2004

(54) SURFACE EVALUATION IN A STAMPING MANUFACTURING PROCESS UTILIZING TRUE REFLECTION LINE METHODOLOGY AND COMPUTER GRAPHICS TECHNOLOGY

(75) Inventors: Yun Lu, Troy, MI (US); Russell J Navarre, Farmington Hills, MI (US); Li Zhang, Rochester Hills, MI (US)

(73) Assignee: DaimlerChrysler Corporation, Auburn Hills, MI (US)

( * ) Notice: Subject to any disclaimer, the term of this patent is extended or adjusted under 35 U.S.C. 154(b) by 814 days.

(21) Appl. No.: 09/633,212

(22) Filed: Aug. 7, 2000

(51) Int. Cl.$^7$ ................................................. G06G 7/48
(52) U.S. Cl. ...................... 703/7; 703/1; 703/2; 700/98; 700/108; 345/419
(58) Field of Search ........................ 703/1–2, 7; 700/98, 700/108; 345/419

(56) References Cited

U.S. PATENT DOCUMENTS

| | | | |
|---|---|---|---|
| 5,742,511 A | * | 4/1998 | Chasse et al. ................. 700/98 |
| 6,035,242 A | * | 3/2000 | Uemura et al. ................ 700/97 |
| 6,353,768 B1 | * | 3/2002 | Karafillis et al. ............. 700/97 |

OTHER PUBLICATIONS

Neumann et al, "New Simple Reflectance Models for Metals and Other Specular Materials," Technical University of Budapest, pp. 1–15 (Jul. 1998) (paper available at http://citeseer.nj.nec.com/163055.html).*

Shirley et al, "A Practitioners' Assessment of Light Reflection Models," Proceedings of Pacific Graphics 97, pp. 1–10 (1997) (paper available at http://citeseer.nj.nec.com/shirley97practitioners.html).*

Beck, Farouki, and Hinds, Surface Analysis Methods, 1986 IEEE CG&A, pp. 18–32, 34–36.

Hagen and Gschwind, Methods for Surface Interrogation, 1990 IEEE, pp. 187–193.

* cited by examiner

*Primary Examiner*—Samuel Broda
(74) *Attorney, Agent, or Firm*—Thomas A. Jurecko

(57) ABSTRACT

The present invention provides a method for evaluating a surface quality of a simulated stamping which includes the steps of obtaining a CAD model of a desired part, calculate and display at least one image of true reflect line on the CAD model, obtaining a blank mesh representative of the part before the part is formed, and processing the blank mesh with a springback simulation software to obtain a deformed finite element analysis springback blank. True reflect lines are then calculated and displayed on the deformed FEA springback blank, and the reflect lines are compared with the true reflect lines on the CAD model to determine variance of the deformed springback blank with the CAD model.

4 Claims, 5 Drawing Sheets

SURFACE EVALUATION IN A STAMPING MANUFACTURING PROCESS UTILIZING TRUE REFLECTION LINE METHODOLOGY AND COMPUTER GRAPHICS TECHNOLOGY

FIELD OF THE INVENTION

The present invention relates to a method of surface evaluation, and more particularly, to a method of surface evaluation which predictively simulates and potentially corrects surface defects of a simulated stamping utilizing a true reflection line methodology and computer graphics technology.

BACKGROUND OF THE INVENTION

In the manufacture of automobiles, the exterior panels of a vehicle are often shaped by a stamping press. Such a stamping press typically incorporates stamping dies and a hydraulic or mechanical press component. In forming, a sheet metal blank is placed between the dies and then the press component is actuated. The dies close and shape the sheet metal blank into the desired shape.

To determine the required die surface, sheet metal blanks are formed with a die having an initial surface. The formed blanks are then evaluated to determine whether the die has the proper shape. If it does not, then the dies are modified based on draw simulation results.

To analyze the resulting shape, reflection machines are often used to check the surface quality of the formed parts. As shown in FIG. 1, reflection machines incorporate a plurality of light bars 10 spaced from each other. The light bars 10 are positioned a predetermined distance away from the panel 12, which is a formed part to be evaluated. An observer at viewpoint 14 observes light reflected by panel 12 which was generated by light bars 10. These reflections are in the form of lines 16. If lines 16 vary from a standard regular pattern, then panel 12 is distorted to some degree from the required configuration, indicating a flaw in the stamping manufacturing process.

While this method adequately allows an individual to determine the accuracy and quality of a manufactured panel, it requires that the die be constructed before it is tested. If the panel does not meet the surface requirement, the die surface must be modified and sometimes reconstructed. This increases the overall manufacturing cost. Specifically, when a stamping die is being designed and tested, it is common that the die does not have the optimum geometry and characteristics to ensure that a formed part has the right surface quality. As a result, if the observer at view point 14 determines that panel 12 has an improper surface quality, the die must be modified and panel 12 must be scrapped. The present invention was developed in light of these drawbacks.

SUMMARY OF THE INVENTION

It is, therefore, an object of the present invention to provide a method for predictively determining surface deviation in a simulated stamping which does not require actually forming parts to determine the surface deviation.

The present invention achieves these and other objective by providing a method for evaluating a surface quality of a desired part having a specific shape which comprises the steps of obtaining a CAD model of the desired part, generating at least one true reflection line on the CAD model. Obtaining a simulated blank mesh using FEA simulation software and processing the blank mesh with a springback simulation software to obtain a finite element analysis (FEA) springback blank. True reflect lines are then generated on the FEA springback blank, and the true reflect lines on the FEA spring back blank are compared with the true reflect lines on the CAD model to determine deviation of the true reflection lines on the springback blank from that of the CAD model.

Additional advantages and features of the present invention will become apparent from the subsequent description and the appended claims taken in conjunction with the accompanying drawings.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
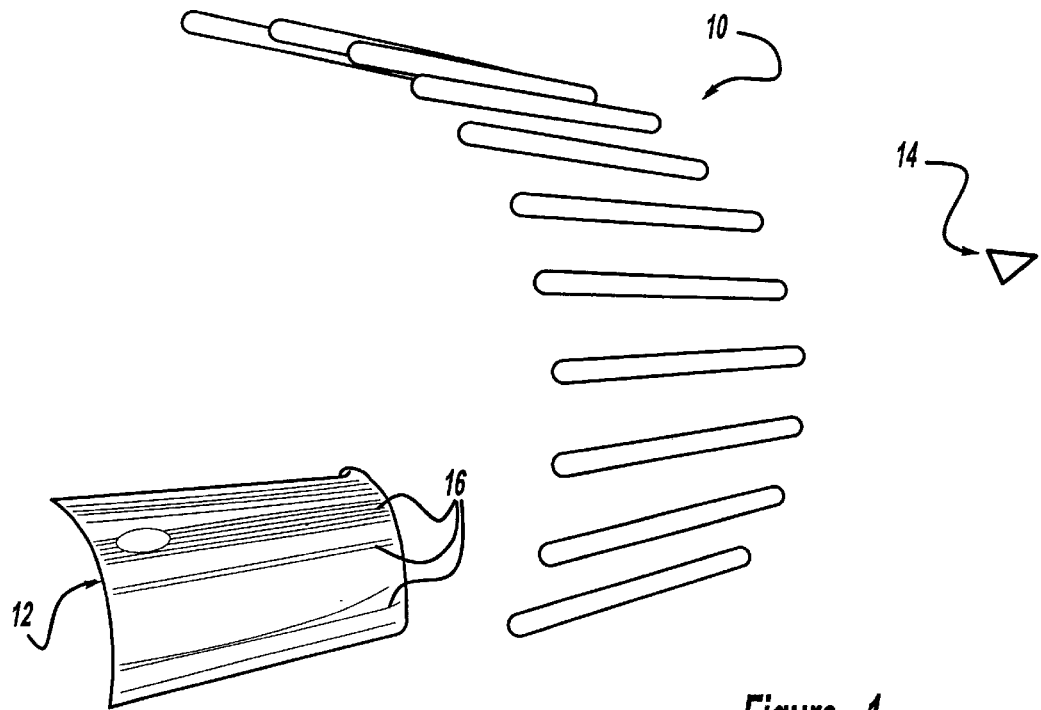
FIG. 1 is a perspective view of a device for evaluating the surface quality of a formed part according to the prior art.

Referring to FIG. 1, a device for evaluating surface quality of a formed part according to the prior art is shown. Here, light bars 10 illuminate rays of light onto panel 12. An observer at view point 14 observes reflected light from panel 12 to determine the surface quality of panel 12. Specifically, light bars 10 create line-like images of true reflect lines 16 on panel 12. The regularity of the lines 16 is what qualifies the panel 12 as having the proper surface quality.

Figure 2:
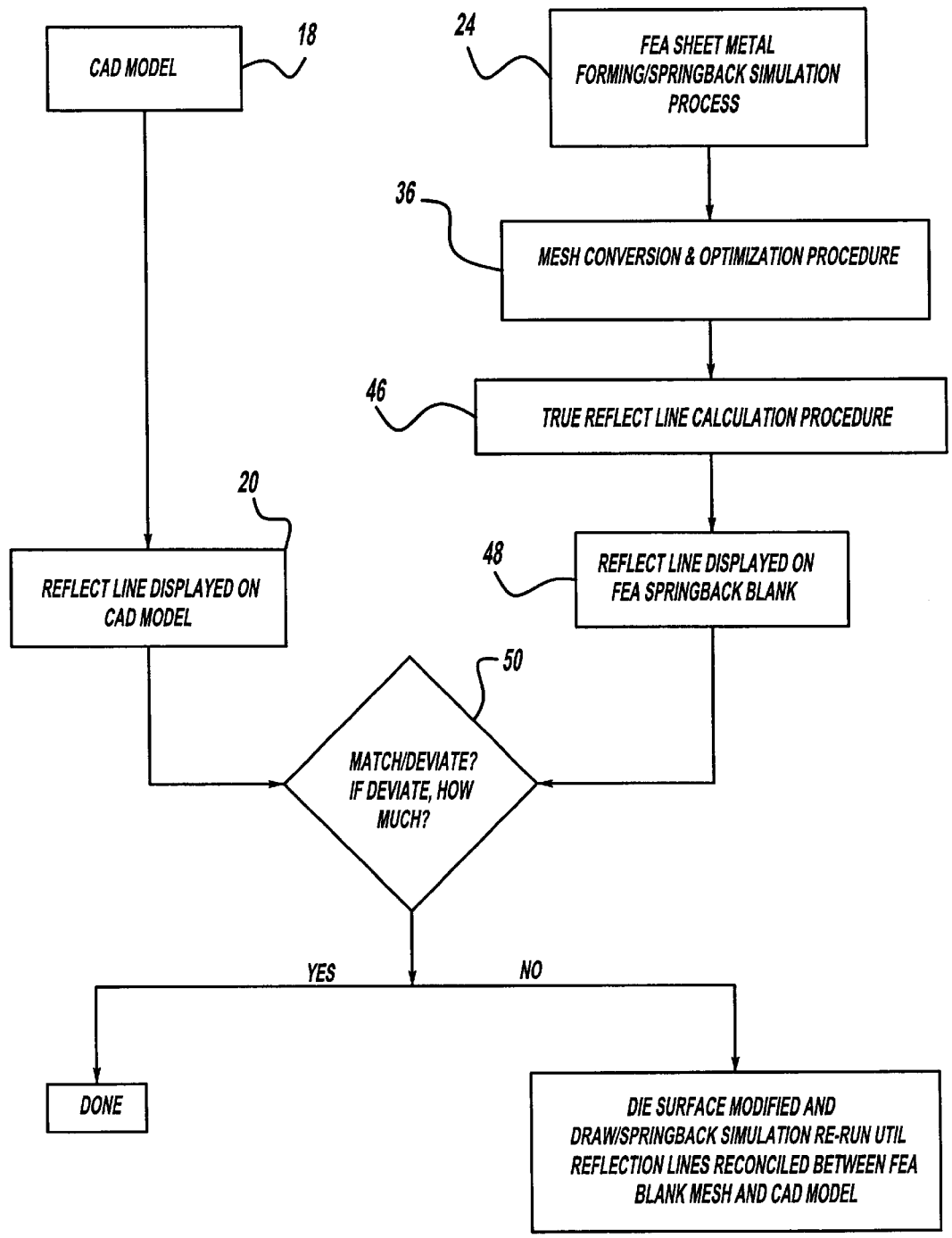
FIG. 2 is a flowchart for a surface evaluation of a stamping manufacturing process utilizing a true reflection line methodology and computer graphics technology according to the principles present invention.

Referring now to FIG. 2, a flowchart of a surface evaluation for a stamping manufacturing process utilizing a true reflection line methodology and computer graphics technology according to the principles of the present invention is shown. In the present invention, a computer generated panel is generated to replace panel 12, and computer generated lines are created to replace lines 16. This procedure is performed for two different scenarios. The first scenario involves generating true reflection lines on a CAD model of a panel designed to the desired specifications of the manufacturer. This first scenario is used as a model or standard. The second scenario involves generating true reflection lines on a simulated panel which is formed from a simulated blank mesh by computer springback simulation software designed to predictively provide a configuration to result in the formation of the panel to the manufacturers specifications.

The true reflection lines from the first scenario are then compared to the true reflection lines from the second scenario to determine if the true reflection lines generated on the simulated panel in the second scenario matches the true reflection lines generated on the CAD model of the first scenario, thereby determining if the finish of the panel of the second scenario matches the finish of the panel in the first scenario.

The surface evaluation flowchart of FIG. 2 begins with block 18 which generates the CAD model template of a panel designed to the desired specifications of the manufacturer, as discussed above using standard CAD software. Here, the CAD model is discretized into triangles.

Figure 3:
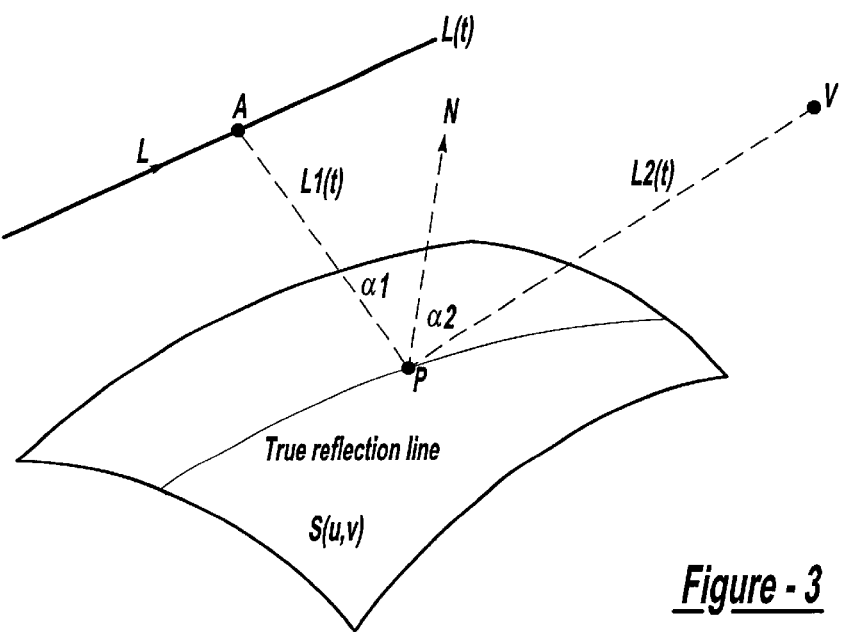
FIG. 3 is a schematic view of a light source, panel and viewer for a method for evaluating surface quality according to the present invention.

Next, in block 20, true reflection lines are calculated and displayed on the CAD model. Referring to FIG. 3, the CAD model true reflection lines are defined as the reflected image of a light source L on the perfectly shining surface S(u,v) of an object observed by a viewer V. A linear light source L is considered here because it simplifies the calculation of the true reflection lines, as depicted in FIG. 3, and is in the context of a linear light source L(t) as it is used in the prior art technique of FIG. 1. Here, $L_1(t)$ is a ray from linear light source L(t) which originates at point A on the light source. $L_2(t)$ is the mirror of the incident ray $L_1(t)$ with respect to the unit surface normal N at the reflection point P for the viewing point V.

The above assumptions establish that vectors $L_1(t)$, $L_2(t)$ and N are coplanar and angle $\alpha_1$ is equal to $\alpha_2$. So, point P is the true reflection point of point A on the linear light source. For every point on the linear light source, the locus of the resulting true reflection points becomes a true reflection line. Since $$\cos(\alpha_1) = \left\langle N, \frac{L_1(t)}{\|L_1(t)\|} \right\rangle \text{ and } \cos(\alpha_2) = \left\langle N, \frac{L_2(t)}{\|L_2(t)\|} \right\rangle,$$

the reflection condition can be mathematically transformed into the following expressions:

$$\frac{L_1(t)}{\|L_1(t)\|} + \frac{L_2(t)}{\|L_2(t)\|} = 2N\left\langle N, \frac{L_1(t)}{\|L_1(t)\|} \right\rangle = 2N\left\langle N, \frac{L_2(t)}{\|L_2(t)\|} \right\rangle$$

where $L_1(t)=P-A$ and $L_2(t)=V-P$, and V is the viewing point. Since the true reflection line is determined by the viewing point, linear light source and the surface normal, it is very sensitive to small deviations of displacement, normal and curvature of the surface of an object. Hence, it is very efficient to detect small offsets of the surface of the object.

Geometric data is supplied by known finite element analysis software. Before visualization and analysis, there are several operations done on the data to make it optimal for rendering and generating reflection lines. The data generally consists of two-dimensional quad elements with no vertex normals. The quads are split into triangles and groups of triangle strips are formed for better rendering performance.

The vertex normals are calculated through a series of steps. Initially, there are three vertices for each triangle and each vertex is assigned the surface normal of the face in which it is contained. Next, vertices that are very close in position and direction of normal are combined and smoothing applied. Each vertex is assigned a normal by taking a weighted average of each of the faces that it is on. Assigning a smooth set of vertex normals to the model is important since the reflect line calculations depend on them. If a surface model was available, the normals could be obtained directly from the equations. However, with a discrete model, only an approximation can be determined.

Figure 4:
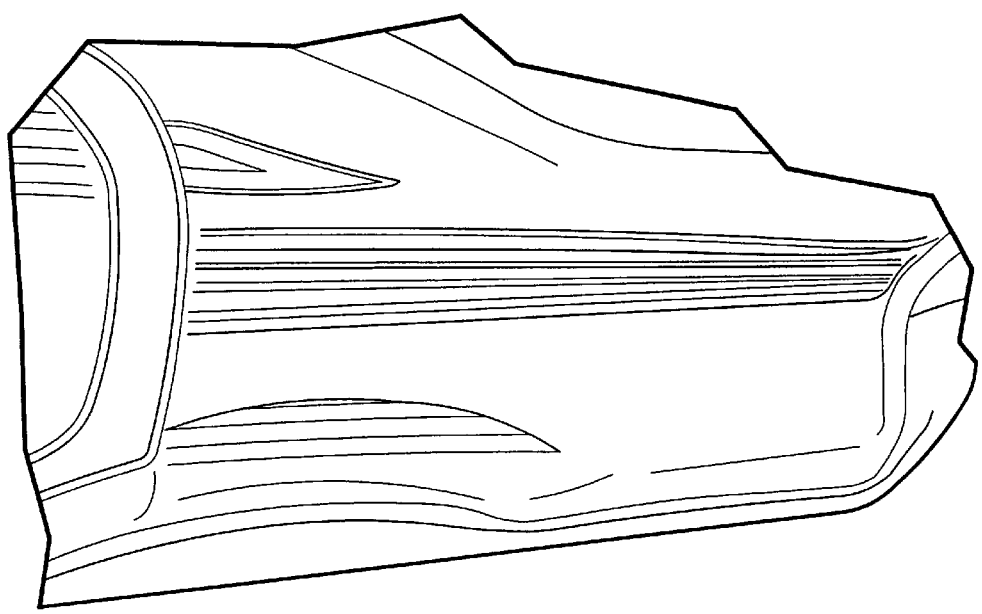
FIG. 4 is a plan view of a CAD model with true reflection lines generated thereon according to one aspect of the present invention.

After the conversion, the CAD model files are in the format of vertex table and face table with connected triangles. Assuming S(u,v) in FIG. 3 is the converted FEA model, to find the true reflection point P on S(u,v), a contouring line algorithm with backward light ray tracing is needed. Assuming P is known as a true reflection point, $L_2(t)$ can be obtained directly since V and P are known. Hence, $L_1(t)$ can be calculated as an explicit function of N from equation (1):

$$L_1 = 2N\left\langle N, \frac{L_2(t)}{\|L_2(t)\|} \right\rangle - \frac{L_2(t)}{\|L_2(t)\|}$$

where L1 is assumed as a unit vector of L1(t). If $L_1(t)$ intersects the given light source L(t) which means the distance between L(t) and $L_1(t)$ is zero, then P is a reflection point with respect to the given light source and viewing point. This distance is called a reflection feature distance or RFD. The equation governing its calculation is:

$$RFD = <L \times L_1 / \|L \times L_1\|, (P-A)>$$

Where L and $L_1$ are the derivatives of the vectors L(t) and $L_1(t)$ respectively. $P-A=L_1(t)$ is known. The zero RFD value $(L(t)-L_1(t))$ can be found using a route searching technique after calculating the RFD value at each vertex in the FEA model. Thus, the CAD model reflection line can be obtained by tracing the locus of the points in the FEA model where RFD values are zero with the given linear light source. As shown in FIG. 4, the CAD model true reflection lines are displayed on the CAD model.

Figure 5:
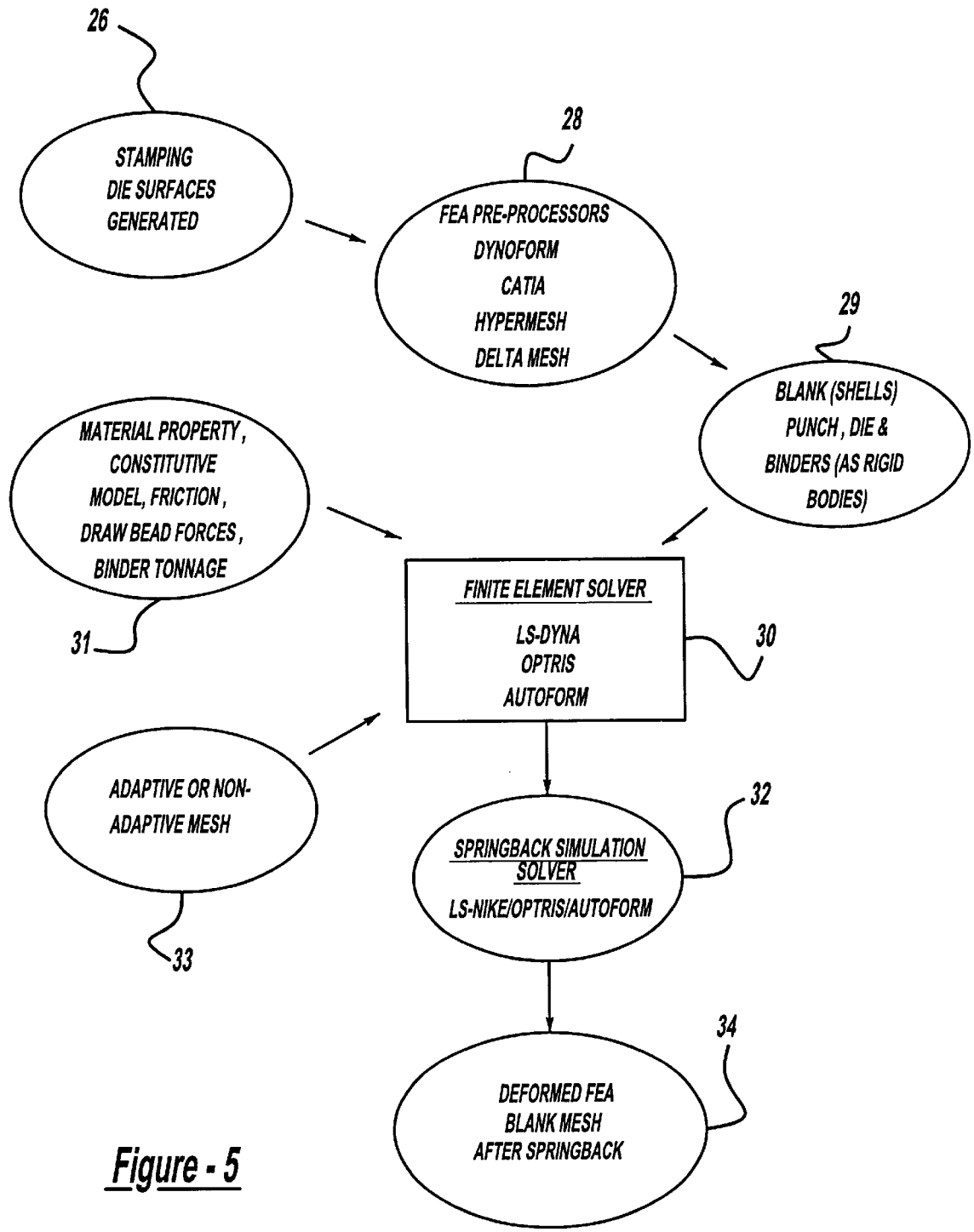
FIG. 5 is a block diagram of a subroutine for processing a simulated blank mesh using spring back simulation software to obtain a finite element analysis springback blank.

On the right side of FIG. 2, in blocks 24, 36, 46, and 48, a computer generation of a simulated panel as would result from forming by a die with specific design characteristics is created and true reflection lines generated. In block 24, a simulation of forming a sheet metal blank into a simulated panel is executed. Referring to FIG. 5, the subroutine governing the procedure in block 24 is depicted. In block 26, die surfaces are generated through CAD software (CATIA or others). Next, in block 28, finite element analysis (FEA) preprocessing software, such as Dynaform/CATIA/ Deltamesh, are used to generate FEA mesh for metal forming simulation. In block 29, using FEA preprocessors, blanks are made as shell elements, and dies and binders are made of rigid bodies. From here, in block 30, a finite element solver such as LS-DYNA, OPTRIS, or Autoform is used to provide finite elements simulation results as applied to the meshed FEA blank. Here, properties such as the material property of the material to be formed, the constitutive model, friction, draw bead forces and binder tonnage are all input into the finite element solver (at block 31) to aid in determining the output shape of the meshed FEA springback blank after it has been stamped with a specific die configuration. Also input into the finite element solver, as depicted at block 33, information is provided as to whether an adaptive or non-adaptive mesh is to be fit to the output of the finite element solver.

After the FEA mesh has been stamped, the proper boundary conditions and trim conditions have been determined, a springback simulation solver in block 32 is used to simulate relaxation stage of the stamping process based on a specific die configuration on the meshed FEA blank having the specific material properties as discussed previously. In block 34, the output of the springback simulation solver from block 32 provides a deformed FEA springback blank mesh which has the configuration resulting from the previously input properties on the FEA blank.

Figure 6:
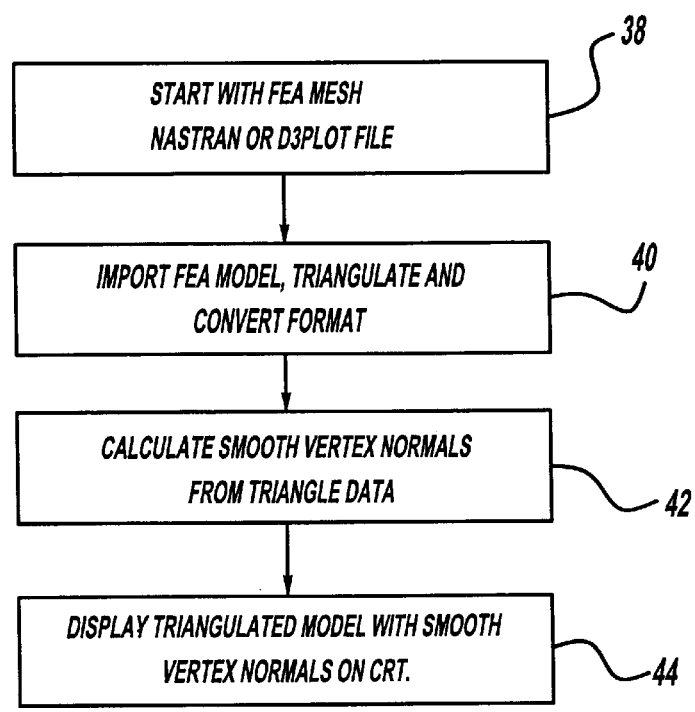
FIG. 6 is flowchart of a software program for conversion and optimization for a method of evaluating a surface quality of a formed part according to the present invention.

Referring back to FIG. 2, a mesh conversion and optimization procedure is performed in block 36 on the deformed FEA blank mesh produced in block 34. This procedure prepares the deformed FEA blank mesh for being fitted with reflect lines. Referring to FIG. 6, the mesh conversion and optimization procedure begins with block 38 where the deformed FEA springback blank mesh is input into conversion and optimization software. Next, the deformed FEA springback blank mesh, which is typically in a rectangular format from the finite element solver and springback simulation solver, is converted into a triangular format. This is done in block 40. The purpose behind this is to standardize the deformed FEA springback blank mesh for comparison with the CAD model (as discussed previously). Next, vertex normals are calculated for each of the vertices of each triangular element and are averaged or thereby smoothed to form a set of smooth vertex normals in block 42. The procedure for these steps is the same as done for the CAD model. The output of this process is shown on a CRT or other display means in block 44.

Figure 7:
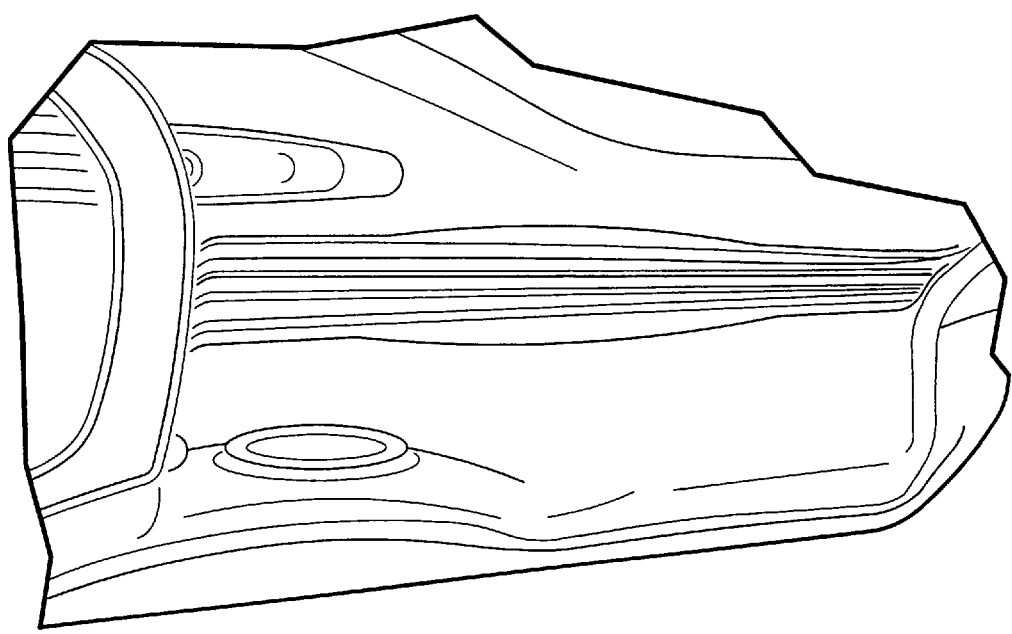
FIG. 7 is a plan view of a simulated stamping with reflect lines displayed thereon according to the principles of the present invention.

Referring back to FIG. 2, true reflect lines are then calculated and displayed on the deformed FEA springback blank in blocks 46 and 48. FIG. 7 shows an example of true reflection lines displayed on a simulated panel. As a result, two separate outputs, one output from block 20 and the other output from block 48, each having a plurality of reflect lines displayed thereon are provided. In block 50, the image reflect lines displayed on the CAD model are compared with the FEA springback reflect lines on the deformed FEA springback blank. The amount of deviation between each reflect line is determined. If this deviation exceeds a predetermined set point or tolerance, then it can be determined that the die surface or characteristics used in the finite element solver in springback simulation of blocks 30 and 32 need to be altered or modified. As such, an operator can then proceed to modify these characteristics and then once again run the software of the present invention to once again determine whether any deviation between the CAD model and the FEA springback blank exist. If the reflect lines from the FEA springback blank vary within the tolerance set out in block 50 with respect to the CAD model, then the die surface suggested in a software program is correct. Therefore, the manufacturer can go ahead and manufacture a finished die product with little concern that the die surface configuration is incorrect.

The invention being thus described, it will be obvious that the same may be varied in many ways. Such variations are not to be regarded as a departure from the spirit and scope of the invention. Such variations or modifications, as would be obvious to one skilled in the art, are intended to be included within the scope of the following claims.

What is claimed is:

1. A method for simulating a stamping and evaluating a surface quality of a simulated part formed using the simulated stamping, said method comprising the steps of:

A. providing a computer model of a desired part;

B. calculate and display at least one image of true reflect line on said computer model;

C. obtaining a finite element analysis springback blank representative of a part before a simulated stamping;

D. processing said finite element analysis springback blank with springback simulation software to obtain a deformed finite element analysis springback blank, said finite element analysis springback software utilizing a plurality of variables to obtain said deformed finite element analysis springback blank, wherein said plurality of variables includes material property, constitutive model, friction, draw bead forces, and binder tonnage;

E. calculate and display true reflect lines on the deformed finite element analysis springback blank; and F. comparing said true reflect line of said deformed finite element analysis springback with said true reflect line on said computer model to determine variance of said deformed finite element analysis springback blank with said computer model.

2. The method according to claim 1, wherein steps A–F are repeated for a second finite element analysis springback blank, wherein at least one of said plurality of variables is modified in response to said variance to generate a second deformed finite element analysis springback blank.

3. The method according to claim 1, wherein said deformed finite element analysis springback blank is triangulated before said true reflect line is calculated for the deformed finite element analysis springback blank.

4. The method according to claim 3, wherein smooth vertex normals are calculated from said triangle data.

* * * * *